(12) United States Patent
Arnett et al.

(10) Patent No.: US 12,414,882 B2
(45) Date of Patent: Sep. 16, 2025

(54) RETRACTABLE SAFETY RESTRAINT (71) Applicants: William Arnett, Muskogee, OK (US); Terry Whitewater, Muskogee, OK (US)

(72) Inventors: William Arnett, Muskogee, OK (US); Terry Whitewater, Muskogee, OK (US)

( * ) Notice: Subject to any disclaimer, the term of this patent is extended or adjusted under 35 U.S.C. 154(b) by 97 days.

(21) Appl. No.: 18/417,076

(22) Filed: Jan. 19, 2024

(65) Prior Publication Data
US 2025/0235363 A1  Jul. 24, 2025

(51) Int. Cl.
A61G 1/044 (2006.01)
A61F 5/37 (2006.01)
A61G 1/04 (2006.01)

(52) U.S. Cl.
CPC ............ *A61G 1/044* (2013.01); *A61F 5/3776* (2013.01); *A61G 1/04* (2013.01); *A61F 5/3769* (2013.01)

(58) Field of Classification Search
CPC . A61G 1/044; A61G 1/04; A61G 7/05; A61G 7/0504; A61F 5/37; A61F 5/3761; A61F 5/3769; A61F 5/3776
USPC ............ 5/628, 625, 658; 128/869, 870, 876
See application file for complete search history.

(56) References Cited

U.S. PATENT DOCUMENTS

| 4,064,574 A * | 12/1977 | Schnitzler | A61G 1/044 5/628 |
|---|---|---|---|
| 5,492,285 A | 2/1996 | Hamrick | |
| D462,710 S | 9/2002 | Babcock | |
| 7,905,233 B2 | 3/2011 | Hopper | |
| 9,016,608 B2 * | 4/2015 | Bradley | B60R 22/36 242/385.4 |
| 9,902,590 B2 * | 2/2018 | Dufek | B65H 75/446 |
| 10,080,693 B1 | 9/2018 | Scheenstra | |
| 10,080,694 B1 * | 9/2018 | Scheenstra | A61G 1/04 |
| 10,335,328 B2 * | 7/2019 | Scheenstra | A61G 1/04 |
| 10,918,540 B2 * | 2/2021 | Scheenstra | A61G 1/044 |
| 11,311,431 B2 * | 4/2022 | Scheenstra | A44B 11/2557 |
| 12,239,565 B2 * | 3/2025 | Oliverio | G16H 70/20 |
| 2008/0251088 A1 * | 10/2008 | Hopper | A61F 5/3776 128/869 |
| 2009/0173354 A1 | 7/2009 | Gold | |
| 2014/0217764 A1 * | 8/2014 | Bradley | A61G 1/044 296/20 |
| 2015/0013690 A1 * | 1/2015 | Dufek | A61F 5/3761 128/879 |
| 2019/0008707 A1 * | 1/2019 | Scheenstra | A61G 1/04 |
| 2019/0350742 A1 * | 11/2019 | Oliverio | G16H 40/63 |
| 2020/0268576 A1 * | 8/2020 | Scheenstra | A44B 11/2557 |
| 2021/0100699 A1 * | 4/2021 | Scheenstra | A61F 5/3776 |
| 2022/0233369 A1 | 7/2022 | Sanders | |

FOREIGN PATENT DOCUMENTS

GB    2563981    1/2019

* cited by examiner

Primary Examiner — Robert G Santos

(57) ABSTRACT

A retractable safety restraint generally comprising a first strap portion, a second strap portion, a buckle, a retractor, and a retractable strap that can be used to securely hold patients on a gurney or stretcher. The retractable design promotes secure and snug holding of a patient. The retractable safety restraint can be temporarily connected to any rail or similar portion of a gurney or stretcher.

11 Claims, 7 Drawing Sheets

RETRACTABLE SAFETY RESTRAINT

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to adjustable straps for gurneys or stretchers and more particularly pertains to a new retractable safety restraint for securing a patient to be transported to a gurney or stretcher.

(2) Description of Related Art Including Information Disclosed Under 37 CFR 1.97 and 1.98

The prior art relates to adjustable straps for gurneys or stretchers which are usually fixed to a gurney or stretcher and are adjustable by hand using a sliding bracket. However, the prior art does not disclose a patient restraint system comprising adjustable straps with mating latch and buckle elements, where the straps are removably attachable to a patient support, such as a gurney or stretcher, and include a retractor mechanism.

BRIEF SUMMARY OF THE INVENTION

An embodiment of the disclosure meets the needs presented above in a retractable safety restraint generally comprising a first strap portion, a second strap portion, a buckle, a retractor, and a retractable strap. The first strap portion is designed to be connected to a gurney and the second strap portion is designed to be connected to a gurney. The buckle includes a male buckle portion and a female buckle portion. The male buckle portion is designed to be inserted into the female buckle portion in a releasable locking engagement. The female buckle portion is attached to the first strap portion. The retractor is attached to the second strap portion. The retractable strap has a first end portion, a body portion, and a second end portion. The first end portion of the retractable strap is attached to an interior portion of the retractor. The body portion of the retractable strap is stored in a coiled manner within the retractor. The retractor includes an aperture. The second end portion of the retractable strap is positioned to project out through the aperture. The male buckle portion is attached to the second end portion of the retractable strap. The retractor is designed to permit a user to pull the male buckle portion and unwind the body portion of the retractable strap until a desired overall length of the retractable safety restraint is achieved that is sufficient to secure a part of a patient to be transported to a gurney and allow the male buckle portion to be connected to the female buckle portion. The retractor is also designed to permit a user to retract the unwound body portion upon disconnection of the male buckle portion from female buckle portion upon completion of use of the retractable safety restraint.

In accordance with at least one possible embodiment, a user, such as an emergency medical services (EMS) worker or a hospital worker, can use the retractable safety restraint to secure a patient to be transported to a gurney. First, the user connects the first strap portion and the second strap portion to a gurney. The user then grasps the retractor attached to the second strap portion and the male buckle portion connected to the end portion of the retractable strap projecting out through the aperture in the retractor. The user then pulls on the male buckle portion and unwinds a body portion of the retractable strap coiled in the retractor until a desired overall length of the retractable safety restraint is achieved that is sufficient to secure a part of the patient to be transported to the gurney and allow the male buckle portion to be connected to a female buckle portion. The user then inserts the male buckle portion into the female buckle portion attached to the first strap portion in a releasable locking engagement. Once the user has transported the patient and/or is otherwise finished using the retractable safety restraint, the user disconnects the male buckle portion from female buckle portion. The unwound body portion is then retracted back into the retractor.

In accordance with at least one possible embodiment, the retractable safety restraint provides a restraining system that is adjustable in size and can be temporarily installed on any portion of any type of gurney or stretcher. In addition, by incorporating a retractor, the retractable safety restraint can be quickly and easily stretched snugly onto a patient, which is important for the safety of the patient. The retractor ensures a snug fit that is not guaranteed with prior art safety straps that must be manually tightened. The retractor also provides storage for the straps and quick removal of the straps. Such easier and faster use is especially important in emergency medical situations where time is of the essence.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

With reference now to the drawings, and in particular to FIGS. 1 through 8 thereof, a new retractable safety restraint embodying the principles and concepts of an embodiment of the disclosure and generally designated by the reference numeral 10 will be described.

Figure 1:
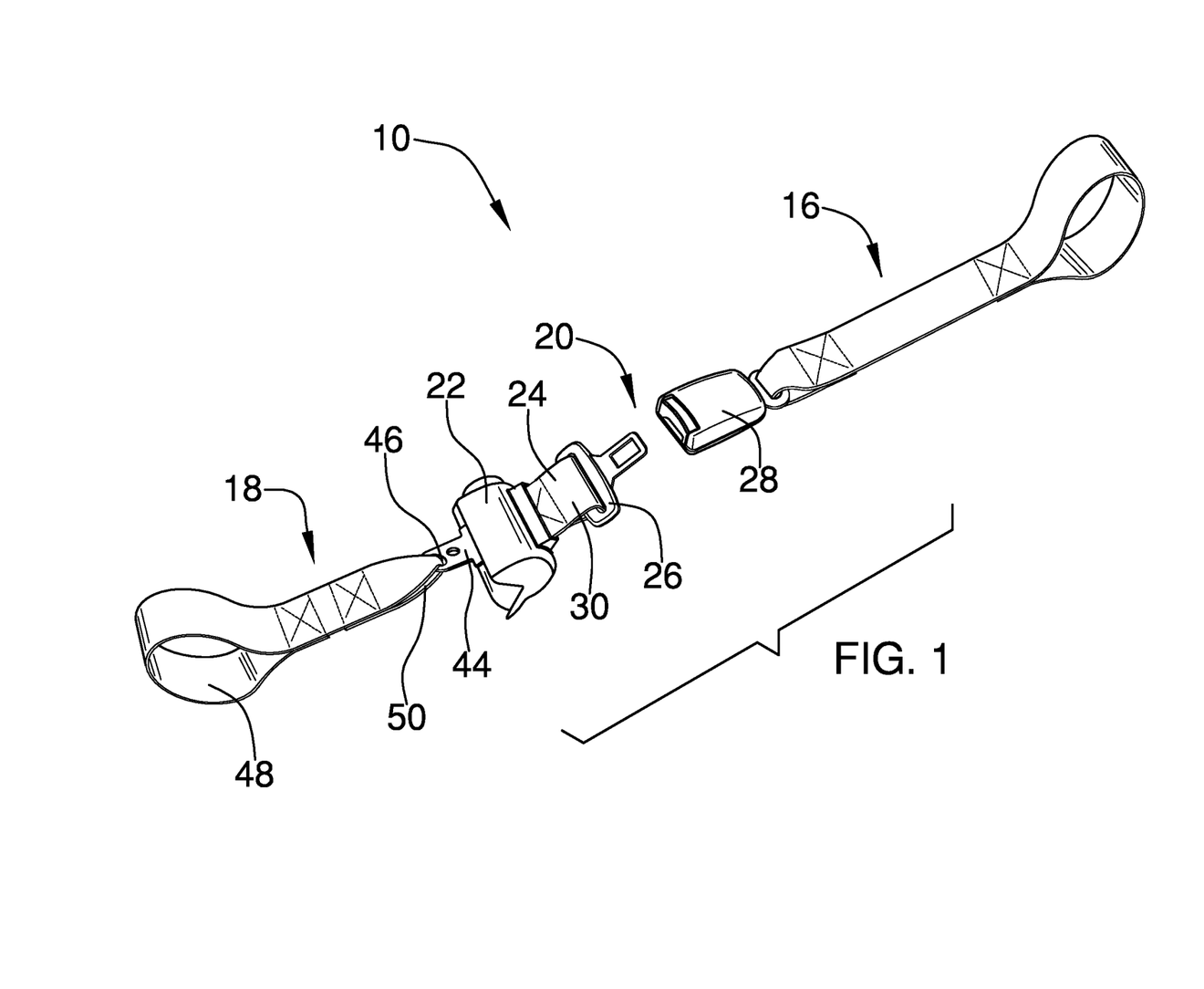
FIG. 1 is a perspective view of a retractable safety restraint according to an embodiment of the disclosure.
Figure 2:
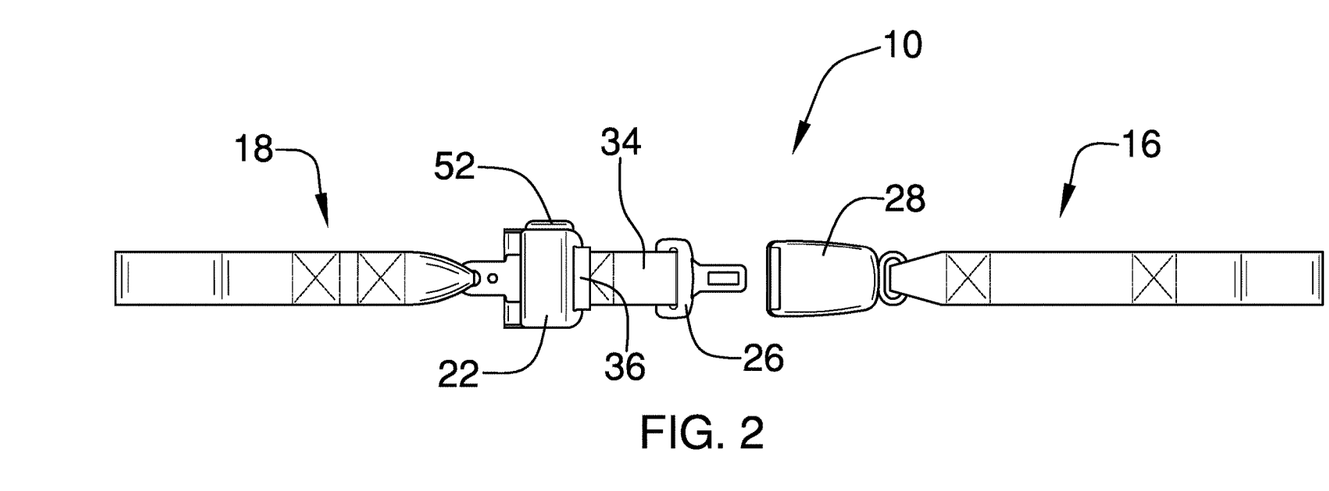
FIG. 2 is a top view of an embodiment of the disclosure.
Figure 3:
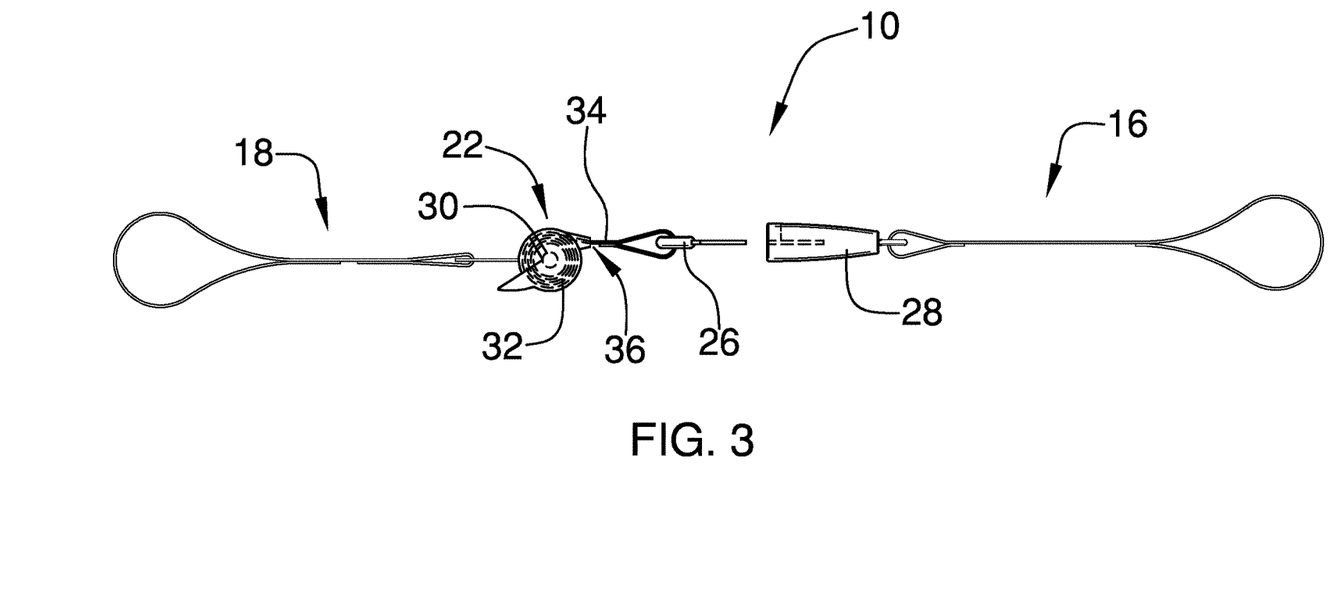
FIG. 3 is a side view of an embodiment of the disclosure.
Figure 4:
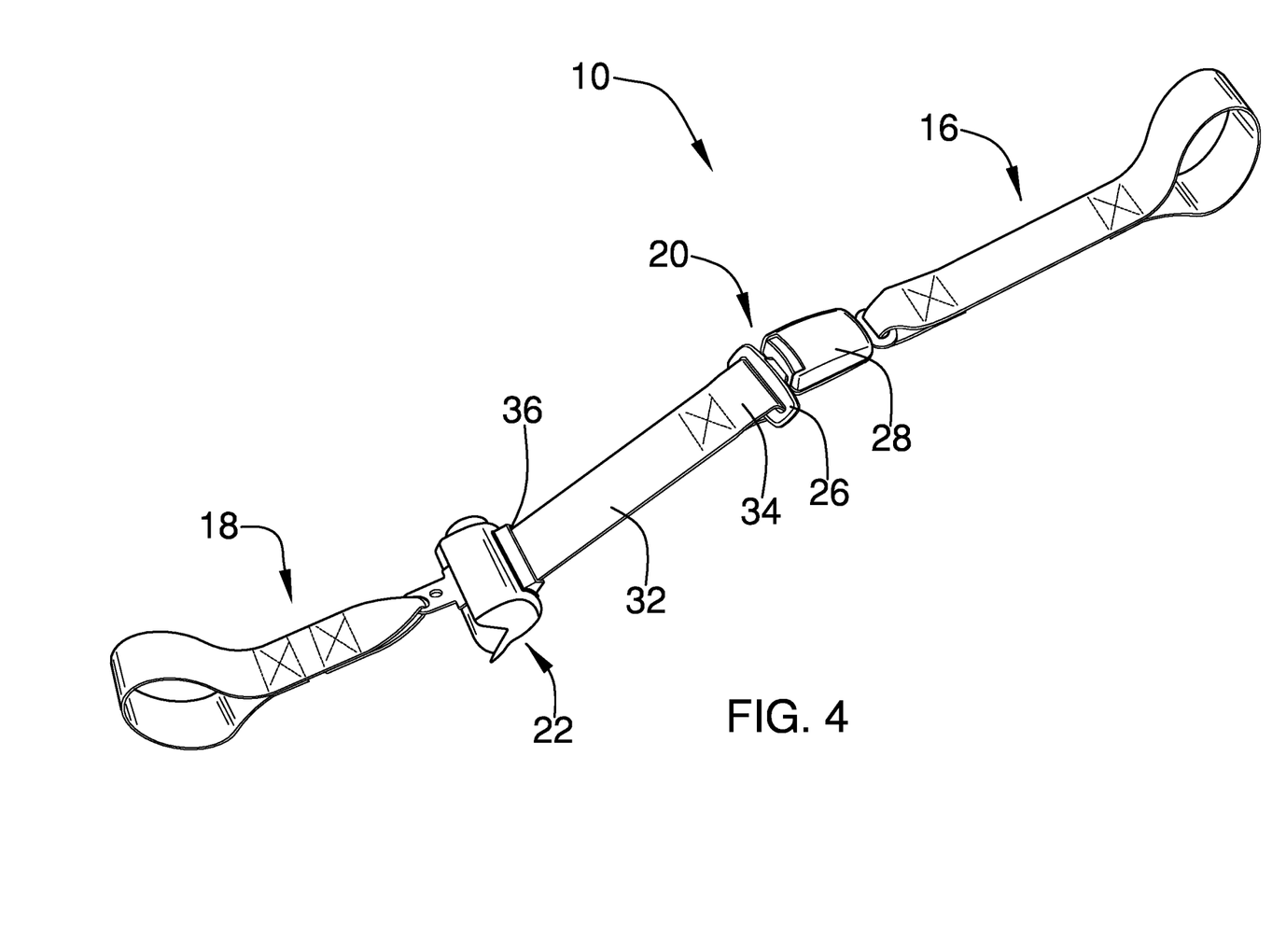
FIG. 4 is a perspective view of an embodiment of the disclosure.
Figure 6:
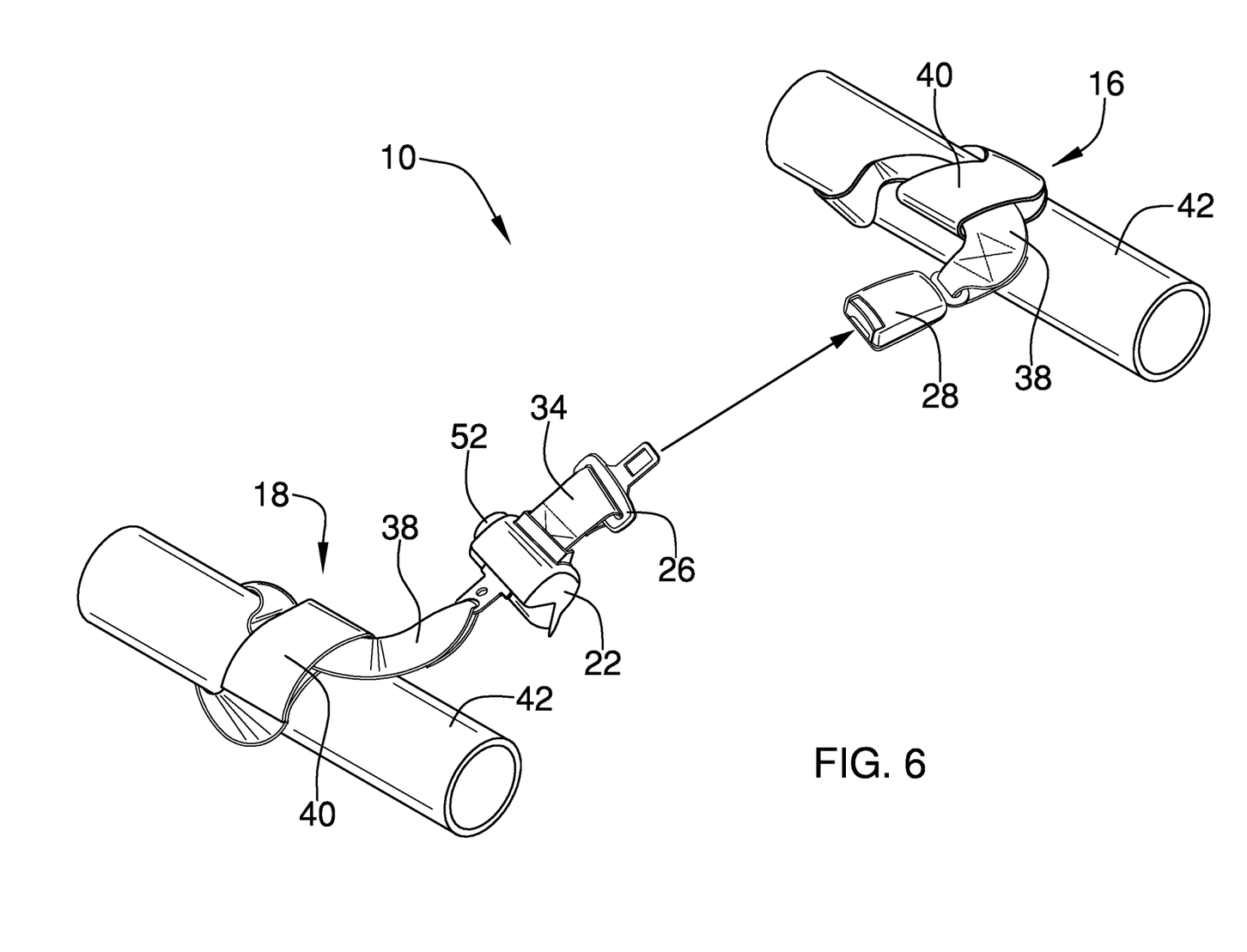
FIG. 6 is a perspective view of an embodiment of the disclosure.
Figure 7:
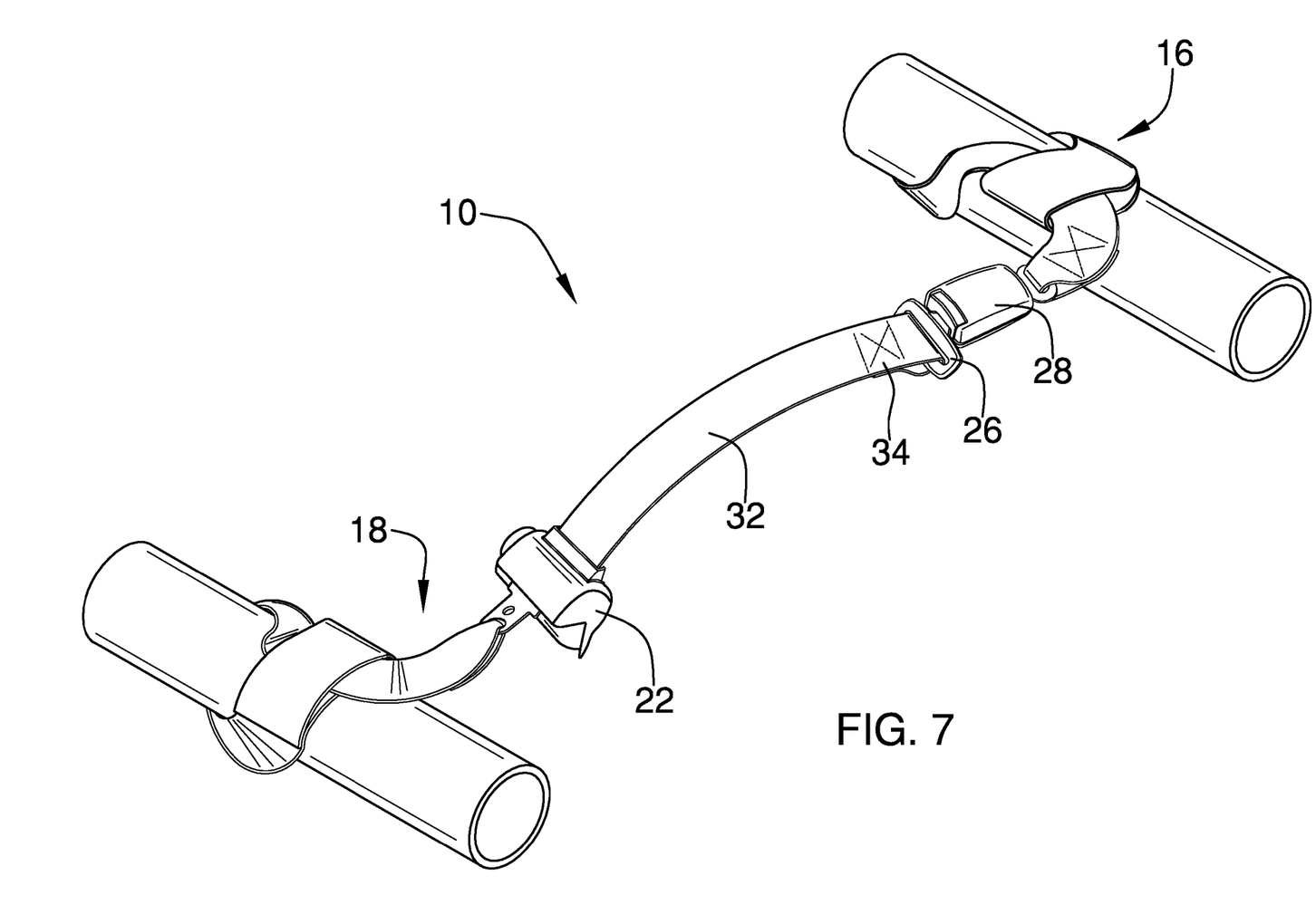
FIG. 7 is a perspective view of an embodiment of the disclosure.
Figure 8:
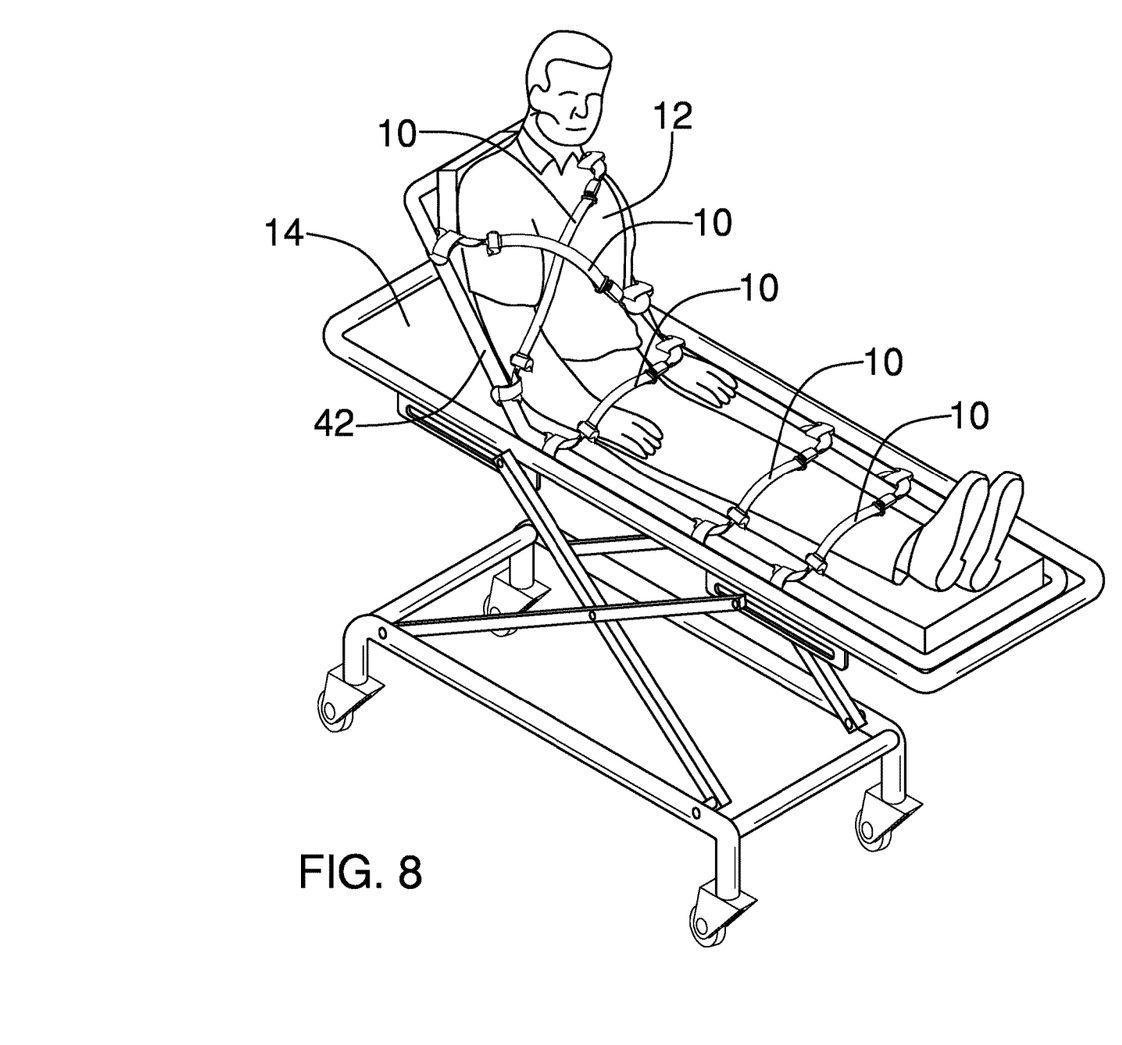
FIG. 8 is a perspective view of an embodiment of the disclosure in use.

As best illustrated in FIGS. 1 through 8, the retractable safety restraint 10 generally comprises a retractable safety restraint 10 to secure a patient 12 to be transported to a gurney 14 (see FIG. 8). As shown in FIGS. 1-7, the retractable safety restraint 10 includes a first strap portion 16, a second strap portion 18, a buckle 20, a retractor 22, and a retractable strap 24. The first strap portion 16 is designed to be connected to a gurney 14 and the second strap portion 18 is designed to be connected to the gurney 14. The buckle 20 includes a male buckle portion 26 and a female buckle portion 28. The male buckle portion 26 is designed to be inserted into the female buckle portion 28 in a releasable locking engagement, as shown in FIG. 4. The female buckle portion 28 is attached to the first strap portion 16. The retractor 22 is attached to the second strap portion 18. As best seen in FIG. 3, the retractable strap 24 has a first end portion 30, a body portion 32, and a second end portion 34. The first end portion 30 of the retractable strap 24 is attached to an interior portion of the retractor 22. The body portion 32 of the retractable strap 24 is stored in a coiled manner within the retractor 22. The retractor 22 includes an aperture 36. The second end portion 34 of the retractable strap 24 is positioned to project out through the aperture 36. The male buckle portion 26 is attached to the second end portion 34 of the retractable strap 24. As shown in FIG. 4, the retractor 22 is designed to permit a user to pull the male buckle portion 26 and unwind the body portion 32 of the retractable strap 24 until a desired overall length of the retractable safety restraint 10 is achieved that is sufficient to secure a part of a patient 12 to be transported to a gurney 14 and allow the male buckle portion 26 to be connected to the female buckle portion 28. The retractor 22 is also designed to permit a user to retract the unwound body portion 32 upon disconnection of the male buckle portion 26 from the female buckle portion 28 upon completion of use of the retractable safety restraint 10.

Figure 5:
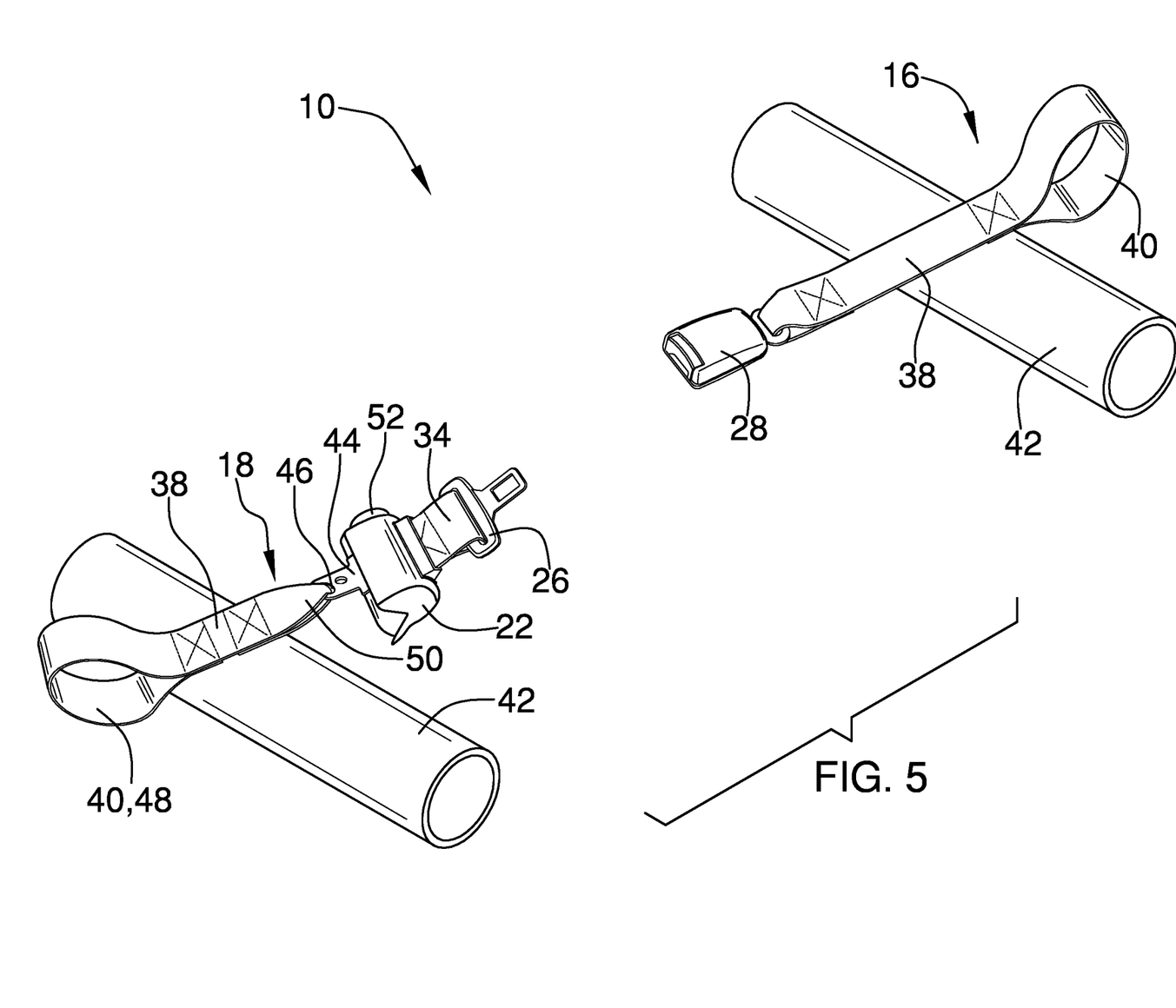
FIG. 5 is a perspective view of an embodiment of the disclosure.

In accordance with at least one possible embodiment, each of the first and second strap portions 16, 18 includes a strap body 38 and a looped end 40. The strap body 38 is designed to be wrapped around a rail 42 or similar portion of a gurney 14 and then inserted through its corresponding looped end 40 (see FIGS. 6 and 7) to releasably secure its corresponding strap portion to the gurney 14. The attachment process is shown in FIGS. 5-7, wherein FIG. 6 shows the retractable strap 24 retracted and FIG. 7 shows the retractable strap 24 unwound to permit connection of the male buckle portion 26 to the female buckle portion 28.

In accordance with at least one possible embodiment, the retractor 22 includes a projection 44 having an opening 46 therein. The looped end 40 of the second strap portion 18 includes a first looped end 48. The second strap portion 18 includes a second looped end 50 opposite the first looped end 48 and interlocked with the projection 44 via the opening 46 therein. The strap body 38 of the first strap portion 16 can also be attached to the female buckle portion 28 in a similar manner.

In accordance with at least one possible embodiment, the retractor 22 is designed to exert a continuous retraction force on the retractable strap 24 to maintain secure and snug engagement with a body part of a patient 12 upon the male buckle portion 26 being connected to the female buckle portion 28, and to automatically retract the retractable strap 24 upon disconnection of the male buckle portion 26 from the female buckle portion 28.

In accordance with at least one possible embodiment, the retractor 22 includes a locking mechanism 52. The locking mechanism 52 is designed to releasably lock the retractable strap 24 in an unwound position upon a user unwinding the retractable strap 24 to a desired overall length of the retractable safety restraint 10. The retractor 22 includes a release mechanism 54 designed to permit a user to release the locking mechanism 52 and retract the retractable strap 24 upon disconnection of the male buckle portion 26 from the female buckle portion 28.

In accordance with at least one possible embodiment, a user, such as an emergency medical services (EMS) worker or a hospital worker, can use the retractable safety restraint 10 to secure a patient 12 to be transported to a gurney 14. First, the user connects the first strap portion 16 and the second strap portion 18 to a gurney 14. The user then grasps the retractor 22 attached to the second strap portion 18 and the male buckle portion 26 connected to the end portion of the retractable strap 24 projecting out through the aperture 36 in the retractor 22. The user then pulls on the male buckle portion 26 and unwinds a body portion 32 of the retractable strap 24 coiled in the retractor 22 until a desired overall length of the retractable safety restraint 10 is achieved that is sufficient to secure a part of the patient 12 to be transported to the gurney 14 and allow the male buckle portion 26 to be connected to a female buckle portion 28. The user then inserts the male buckle portion 26 into the female buckle portion 28 attached to the first strap portion 16 in a releasable locking engagement. Once the user has transported the patient 12 and/or is otherwise finished using the retractable safety restraint 10, the user disconnects the male buckle portion 26 from female buckle portion 28. The unwound body portion 32 is then retracted back into the retractor 22.

In accordance with at least one possible embodiment, in order to connect the first and second strap portions 16, 18 to a gurney 14, the user wraps the strap body 38 around the rail 42 or similar portion of the gurney 14 and then inserts the strap body 38 through a corresponding looped end 40 to releasably secure its corresponding strap portion 16, 18 to the gurney 14.

In accordance with at least one possible embodiment, the retractor 22 can exert a continuous retraction force on the retractable strap 24 and automatically retract the retractable strap 24 upon disconnection of the male buckle portion 26 from the female buckle portion 28.

In accordance with at least one possible embodiment, alternatively the user can unwind the retractable strap 24 and then lock the retractable strap 24 in its unwound position using the locking mechanism 52 of the retractor 22. When the user wants to retract the unwound body portion 32 back into the retractor 22, the user can activate the release mechanism 54 of the retractor 22, such as by pressing a push button, and release the locking mechanism 52 to permit the retractor 22 to retract the unwound body portion 32.

FIG. 8 shows the patient 12 secured to the gurney 14 using multiple retractable safety restraints 10, which are connected to rails 42 at various points thereof.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A retractable safety restraint to secure a patient to be transported to a gurney comprising:
    a first strap portion configured to be connected to a gurney;
    a second strap portion configured to be connected to a gurney;
    a buckle comprising a male buckle portion and a female buckle portion;
    said male buckle portion being configured to be inserted into said female buckle portion in a releasable locking engagement;
    said female buckle portion being attached to said first strap portion;
    a retractor being attached to said second strap portion;
    a retractable strap having a first end portion, a body portion, and a second end portion;
    said first end portion of said retractable strap being attached to an interior portion of said retractor;
    said body portion of said retractable strap being stored in a coiled manner within said retractor;
    said retractor comprising an aperture;
    said second end portion of said retractable strap being disposed to project out through said aperture;
    said male buckle portion being attached to said second end portion of said retractable strap;
    said retractor being configured to permit a user to pull said male buckle portion and unwind said body portion of said retractable strap until a desired overall length of the retractable safety restraint is achieved that is sufficient to secure a part of a patient to be transported to a gurney and allow said male buckle portion to be connected to said female buckle portion; and
    said retractor being configured to permit a user to retract said unwound body portion upon disconnection of said male buckle portion from female buckle portion upon completion of use of the retractable safety restraint.

2. The retractable emergency safety restraint of claim 1, wherein each of said first and second strap portions comprises:
    a strap body;
    a looped end; and
    said strap body is configured to be wrapped around a rail or similar portion of a gurney and then inserted through its corresponding looped end to releasably secure its corresponding strap portion to the gurney.

3. The retractable emergency safety restraint of claim 2, wherein:
    said retractor comprises a projection having an opening therein;
    said looped end of said second strap portion comprises a first looped end; and
    said second strap portion comprises a second looped end opposite said first looped end and interlocked with said projection via the opening therein.

4. The retractable emergency safety restraint of claim 2, wherein said retractor is configured to exert a continuous retraction force on said retractable strap to maintain secure and snug engagement with a body part of a patient upon said male buckle portion being connected to said female buckle portion, and to automatically retract said retractable strap upon disconnection of said male buckle portion from said female buckle portion.

5. The retractable emergency safety restraint of claim 2, wherein:
    said retractor comprises a locking mechanism;
    said locking mechanism is configured to releasably lock said retractable strap in an unwound position upon a user unwinding said retractable strap to a desired overall length of the retractable safety restraint; and
    said retractor comprises a release mechanism configured to permit a user to release said locking mechanism and retract said retractable strap upon disconnection of said male buckle portion from said female buckle portion.

6. The retractable emergency safety restraint of claim 1, wherein said retractor is configured to exert a continuous retraction force on said retractable strap to maintain secure and snug engagement with a body part of a patient upon said male buckle portion being connected to said female buckle portion, and to automatically retract said retractable strap upon disconnection of said male buckle portion from said female buckle portion.

7. The retractable emergency safety restraint of claim 1, wherein:
    said retractor comprises a locking mechanism;
    said locking mechanism is configured to releasably lock said retractable strap in an unwound position upon a user unwinding said retractable strap to a desired overall length of the retractable safety restraint; and
    said retractor comprises a release mechanism configured to permit a user to release said locking mechanism and retract said retractable strap upon disconnection of said male buckle portion from said female buckle portion.

8. A method of using a retractable safety restraint to secure a patient to be transported to a gurney comprising the steps of:
    connecting a first strap portion to a gurney;

connecting a second strap portion to a gurney;

grasping a retractor attached to said second strap portion and a male buckle portion connected to an end portion of a retractable strap projecting out through an aperture in said retractor;

pulling on said male buckle portion and unwinding a body portion of said retractable strap coiled in said retractor until a desired overall length of the retractable safety restraint is achieved that is sufficient to secure a part of a patient to be transported to a gurney and allow said male buckle portion to be connected to a female buckle portion;

inserting said male buckle portion into said female buckle portion attached to said first strap portion in a releasable locking engagement;

disconnecting said male buckle portion from female buckle portion upon completion of use of the retractable safety restraint; and retracting said unwound body portion back into said retractor.

9. The method of claim 8, wherein said steps of connecting said first and second strap portions to a gurney comprise wrapping a strap body around a rail or similar portion of a gurney and then inserting said strap body through a corresponding looped end to releasably secure its corresponding strap portion to the gurney.

10. The method of claim 8, wherein said step of retracting said unwound body portion back into said retractor comprises said retractor exerting a continuous retraction force on said retractable strap and automatically retracting said retractable strap upon disconnection of said male buckle portion from said female buckle portion.

11. The method of claim 8, wherein:

said step of unwinding said body portion of said retractable strap comprises locking said retractable strap in its unwound position using a locking mechanism of said retractor; and said step of retracting said unwound body portion back into said retractor comprises activating a release mechanism of said retractor and releasing said locking mechanism to permit said retractor to retract said unwound body portion.

* * * * *